(12) United States Patent
Martin et al.

(10) Patent No.: US 12,324,864 B2
(45) Date of Patent: Jun. 10, 2025

(54) SANITIZING WIPE WITH METAL DETECTABLE PRINTED INDICIA

(71) Applicant: Illinois Tool Works Inc., Glenview, IL (US)

(72) Inventors: Robert Martin, Glenview, IL (US); Paul Richard Jelonek, Geneva, IL (US)

(73) Assignee: Illinois Tool Works Inc., Glenview, IL (US)

( * ) Notice: Subject to any disclaimer, the term of this patent is extended or adjusted under 35 U.S.C. 154(b) by 998 days.

(21) Appl. No.: 16/924,268

(22) Filed: Jul. 9, 2020

(65) Prior Publication Data

US 2021/0008238 A1 Jan. 14, 2021

Related U.S. Application Data

(60) Provisional application No. 62/873,074, filed on Jul. 11, 2019.

(51) Int. Cl.
*A61L 2/18* (2006.01)
*A61L 2/28* (2006.01)
(Continued)

(52) U.S. Cl.
CPC ................ *A61L 2/18* (2013.01); *A61L 2/28* (2013.01); *C09D 11/023* (2013.01);
(Continued)

(58) Field of Classification Search
CPC ......... A61L 2/18; C09D 11/52; A61K 8/0208; G01V 15/00; A61F 13/44; A61F 13/00059; A61F 2013/00153; A61F 2013/15243; A61F 13/51394; C11D 17/04; C11D 17/049; G01R 33/028
See application file for complete search history.

(56) References Cited

U.S. PATENT DOCUMENTS 3,396,419 A * 8/1968 Richter ............... A47K 7/03
15/104.93
3,422,816 A * 1/1969 Palfrey ............... A61B 5/06
604/362

(Continued)

FOREIGN PATENT DOCUMENTS

CA 1239379 A * 7/1988 ............ A61B 50/37
GB 1381855 A * 1/1975 ............ A61L 15/18
(Continued)

OTHER PUBLICATIONS

Int'l Search Report and Written Opn. issued in PCT/US2020/041486, dated Dec. 11, 2020.

*Primary Examiner* — Jennifer A Gillett
(74) *Attorney, Agent, or Firm* — MaxGoLaw PLLC

(57) ABSTRACT

An article is provided having a substrate with an indicia printed on the substrate, where the indicia is printed with an ink that is detectable by in-line manufacturing production X-ray, metal, or magnetic detectors. A package for multiple such articles is also provided. A process for detecting a sanitizable substrate wipe with magnetic, metal, or X-ray detection equipment in a production setting is also provided. With process implementation article loss in a product can be detected thereby reducing precautionary product discard.

14 Claims, 2 Drawing Sheets

(51) Int. Cl.
  *B65B 5/06* (2006.01)
  *B65B 55/22* (2006.01)
  *B65B 57/18* (2006.01)
  *C09D 11/023* (2014.01)
  *C09D 11/106* (2014.01)
(52) U.S. Cl.
  CPC ......... *C09D 11/106* (2013.01); *A61L 2202/15* (2013.01); *A61L 2202/20* (2013.01); *B65B 5/06* (2013.01); *B65B 55/22* (2013.01); *B65B 57/18* (2013.01)

(56) References Cited

U.S. PATENT DOCUMENTS

| | | | | |
|---|---|---|---|---|
| 3,456,867 | A * | 7/1969 | Repko | B65D 75/5827 383/203 |
| 3,857,677 | A * | 12/1974 | Moore | A23L 3/00 53/425 |
| 4,323,904 | A * | 4/1982 | Edwards | G03G 19/00 346/74.7 |
| 5,045,080 | A * | 9/1991 | Dyer | A61F 13/44 604/362 |
| 5,897,673 | A | 4/1999 | Nishida et al. | |
| 8,980,982 | B2 | 3/2015 | Martin et al. | |
| 2005/0096614 | A1 * | 5/2005 | Perez | A61F 13/472 604/378 |
| 2005/0160543 | A1 * | 7/2005 | Catalfamo | A47L 13/17 15/104.93 |
| 2008/0142023 | A1 * | 6/2008 | Schmid | A61L 31/16 128/849 |
| 2009/0014518 | A1 * | 1/2009 | Stewart | G06Q 10/30 235/385 |
| 2012/0235078 | A1 * | 9/2012 | Iftime | C09D 11/322 252/62.54 |
| 2012/0241589 | A1 * | 9/2012 | Martin | H01F 1/01 524/556 |
| 2012/0259302 | A1 * | 10/2012 | Chaisumdet | A61F 13/36 264/172.19 |
| 2013/0193249 | A1 * | 8/2013 | Orozco Ramirez | B65H 18/28 242/525 |
| 2017/0073535 | A1 * | 3/2017 | Kusukame | C09D 11/107 |
| 2017/0156336 | A1 * | 6/2017 | Joshi | A61L 2/235 |
| 2018/0332874 | A1 * | 11/2018 | Kelley | C11D 3/3947 |
| 2019/0255203 | A1 * | 8/2019 | Fukuzaki | A61L 2/235 |
| 2021/0177218 | A1 * | 6/2021 | Jin | A01N 25/34 |

FOREIGN PATENT DOCUMENTS

| | | | |
|---|---|---|---|
| WO | 20050072594 A1 | 8/2005 | |
| WO | WO-2015073166 A1 * | 5/2015 | ............... D01F 1/10 |
| WO | 20170048897 A1 | 3/2017 | |
| WO | WO-2018056365 A1 * | 3/2018 | ............. A01N 59/00 |

* cited by examiner

SANITIZING WIPE WITH METAL DETECTABLE PRINTED INDICIA

RELATED APPLICATIONS

This application claims priority benefit of U.S. Provisional Ser. No. 62/873,074 filed Jul. 11, 2019; the contents of which is hereby incorporated by reference.

FIELD OF THE INVENTION

The present invention relates to the technical field of composite fibers, and in particular to sanitizing wipes and other articles with printed indicia that are X-ray, metal detectable, or magnetic detectable.

BACKGROUND OF THE INVENTION

Servicing of a food or pharmaceutical production line currently has strict guidelines that require exclusion zones from which various material packaging components and accessories are excluded. In spite of these exclusion policies, plastic debris does enter production lines and with even a single piece of plastic entering a production stream, large quantities of otherwise usable product must be discarded. Rules regarding processing of ground meat are exemplary of those that require discard of the product if possibly contaminated. Common plastic packaging or service articles that are inadvertently brought into production exclusion zones include aerosol cans, grease cartridge tubes, grease tube caps, plastic fiber toweling, packing straps, pail lids, jar caps, and personal protective clothing.

Metal detectors are commonly found on food processing lines to assure that metal shards that represent a laceration hazard do not end up in food products. Similarly, pharmaceutical and biomedical device production are also vulnerable to not only the hazards associated with metal debris ending up in product streams, but also the prospect that such metal can degrade active pharmaceutical ingredients or serve as a potential source of infection. Numerous technologies are known to the art to detect spurious metal within a production line. These technologies include a transmitter coil-receiver coils for metal detection systems, systems that use radio frequencies, and magnetic field based systems. In recognition of the fact that some metallic materials are not ferromagnetic and simultaneously not particularly good electrical conductors, x-ray scanners and other electromagnetic field (emf) spectral region spectral detection techniques have been added to food and pharmaceutical product lines to facilitate the detection of a wider range of contaminants.

Many industries have a need for metal detectable polymers and articles made therefrom. By way of example, a food, medical, or pharmaceutical production line maintains tight audit control of service items that enter the manufacturing facility to assure such items do not accidently enter the production stream as a contaminant that can be fragmented into dangerous shards. Historically, plastics have been precluded from some environments due to the inability to locate such articles with product screening X-ray or magnetic detectors. Recently, plastic articles have been developed that are filled with metal particulate or barium sulfate, as detailed in U.S. Pat. No. 8,980,982 that are detectable with magnetic or X-ray detectors, yet still process as injection moldable thermoplastics and operate in a manner similar to their unfilled conventional counterparts. By way of example, U.S. Pat. No. 5,897,673 teaches fibers containing fine metallic particles that are cross-linked to the polymeric fiber.

A wet wipe is a moistened piece of paper or plastic cloth that often comes folded, individually wrapped, or spooled into a perforated roll in a canister for convenience. Wet wipes are used for cleaning purposes illustratively including personal hygiene and surface cleaning. Industrial-strength cleaning wipes are pre-impregnated with powerful cleaning fluids that cut through the dirt as the high performance fabric absorbs the residue. Industrial wipes have the ability to clean a vast range of tough substances from hands, tools and surfaces, including: grime, grease, oil and water-based paints and coatings, adhesives, silicone and acrylic sealants, poly foam, epoxy, oil, tar and more. Medical wet wipes are available for various applications including alcohol wet wipes, chlorhexidine wipes (for disinfection of surfaces and noninvasive medical devices) and sporicidal wipes. Medical wipes can be used to prevent the spread of pathogens such as the Norovirus and *Clostridium Difficile*.

Wet wipes have a substrate that is produced as air-laid paper, the fibers are carried and formed to the structure of paper by air or with nonwoven, spun-lace fabric; or more commonly today as plastic textiles made of polyester or polypropylene. Nonwoven fabric is a fabric-like material made from staple fiber (short) and long fibers, bonded together by chemical, mechanical, heat or solvent treatment, which are neither woven nor knitted. The spun-lace process is a nonwovens manufacturing system that employs jets of water to entangle fiber and thereby provide fabric integrity. Melt blowing is a fabrication method where a polymer melt is extruded through small nozzles surrounded by high speed blowing gas. The randomly deposited fibers form a nonwoven sheet product.

The material that forms the substrate of the wipe is moistened with water, disinfectants, or other liquids (e.g., isopropyl alcohol) depending on the applications. The wipe is rendering sanitizing through inclusion of antimicrobial compounds that illustratively quaternary ammonium compounds, triclosan, triclocarban, hypochlorite, quat-alcohols, chloroxylenol, or combinations thereof. A wipe sanitizing solution also further includes softeners, lotions, or perfume to adjust the tactile properties. Preservatives such as methylisothiazolinone are used to prevent bacterial or fungal growth in the package. There components have traditionally been incompatible with iron-based pigments.

By way of example various wipes, scrub pads, hair covers, suits, aprons, shoe covers, and other manufacturing aids or personal protective equipment could allow better quality control of manufacturing with less stringent audit processes if any such articles lost in a production stream could be detected by X-ray, metal detector, or magnetic anomaly.

There continues to be a need for production of various articles from that have the added benefit of being X-ray or magnetically detectable while operating in a manner similar to conventional articles.

SUMMARY OF THE INVENTION

An article is provided with a substrate and an indicia printed on the substrate, the indicia printed with an ink that is detectable by X-ray, metal, or magnetic detectors. The ink is made detectable with the inclusion of iron, bronze, brass, steel, barium salts, cobalt, titanium, tin, aluminum, copper, tungsten, platinum, silver, bismuth, zinc, lead, molybdenum, neodymium, samarium, alloys of any of the aforementioned, oxides of any of the aforementioned metals, nitrides of any of the aforementioned. The article is formed as a nonwoven material that is spun-laced, melt blown, spunbond, or a composite of two or more of these fiber formations. Properties imparted to the article may include electromagnetic spectral detectability, thereby making the articles suitable for usage in a variety of fields including food production, medical, and pharmaceutical production environments.

A process for detecting an article in a production area containing magnetic, metal, or X-ray detection equipment is also provided. With process implementation article loss in a product can be detected thereby reducing precautionary product discard.

BRIEF DESCRIPTION OF THE DRAWINGS

The present invention is further detailed with respect to the following figures that depict various aspects of the present invention.

DETAILED DESCRIPTION OF THE PREFERRED EMBODIMENTS

Figure 1:
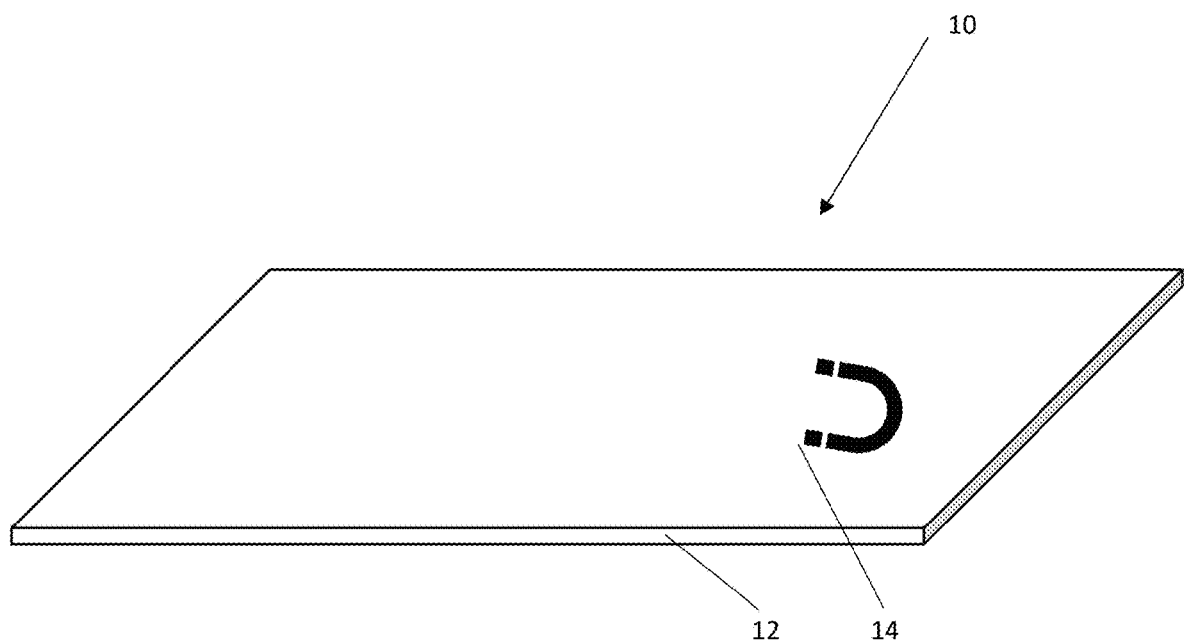
FIG. 1 is a perspective view of a wipe with metal detectable printed indicia on the surface thereof.

The present invention has utility as sanitizing wipes and other articles that have printed indicia on a surface thereof, the indicia being X-ray, metal, or magnetic detectable with conventional industrial detection equipment. The printed indicia are rendered with iron rich ink that makes the printed article detectable in an industrial metal detector in a food, pharmaceutical, or other production environment. The detectable ink operative herein illustratively iron, bronze, brass, steel, barium salts, cobalt, titanium, tin, aluminum, copper, tungsten, platinum, silver, bismuth, zinc, lead, molybdenum, neodymium, samarium, alloys of any of the aforementioned, oxides of any of the aforementioned metals, nitrides of any of the aforementioned. A detectable ink may be applied illustratively by screen printing, feso printing, or ink jet printing. Embodiments of the inventive wipe may be used for food grade hand cleaning wipes or any other dry or wet wipe used in these types of facilities where a need exists to be able to detect a lost foreign object such as a wipe. By way of example, an inventive wipe is detected by a metal detector orthogonal response on a Loma IQ3+ balanced coil metal detector as a single ply. The substrate of the sanitizing wipe in specific inventive embodiments may be formed as a nonwoven material that is spun-laced, melt blown, spunbond, or a composite of two or more of these fiber formations.

In contrast to conventional inks, that include metal or metal oxide particulate, the present invention includes loadings that are sufficient to be detected by conventional in-line metal detection equipment and in some inventive embodiments are compatible with prolonged storage exposure to sanitizing solutions absorbed within such a wipe.

As used herein, the term "fiber" defines both fibers of finite length, such as conventional preselected length fiber, as well as substantially continuous structures, such as continuous filaments, unless otherwise indicated. The fibers of the present invention are appreciated to be hollow or solid fibers, and further can have a substantially round or circular cross-section or cross-sections of different symmetry space groups with other cross-sections illustratively including oval; lobular; polygonal such as triangular, square, rectangular, trapezoidal, pentagonal, and hexagonal. A fiber of the present invention in some embodiments has a sheath that varies in polymer or particulate, with the variation being as to composition or concentration, or both such properties.

As used herein, the term "multi-component fibers" is defined to include preselected length fiber and continuous filaments with two or more discrete structured domains of deliberately different composition or component concentration and is intended to specifically include sheath/core and island configurations.

As used herein, the term "yarn" defines multiple fibers wound together into a single continuous strand.

It is to be understood that in instances where a range of values are provided that the range is intended to encompass not only the end point values of the range but also intermediate values of the range as explicitly being included within the range and varying by the last significant figure of the range. By way of example, a recited range of from 1 to 4 is intended to include 1-2, 1-3, 2-4, 3-4, and 1-4.

It is appreciated that both the cross-sectional shape of the fiber and the configuration of the particulate and other components therein depends upon the equipment that is used in the preparation of the fiber, the process conditions, and the melt viscosities of the various components. A wide variety of fiber configurations are operative according to the present invention to achieve loadings sufficient for magnetic or X-ray detection. These illustratively include woven, nonwoven, and lofted substrates.

The polymeric component of the fiber is readily selected from any of the types of polymers known in the art that are capable of being formed into fibers, including polyolefins, polyvinyl, polyvinyl alcohol, polyesters, polyamides, copolymers containing any of the aforementioned polymers as blocks of a copolymer, and combinations thereof. Specific polyolefins operative herein illustratively include polypropylene; polyethylene; polybutene; and polyisobutylene; polyamides such as NYLON 6 and NYLON 6,6; polyacrylates; polystyrenes; polyurethanes; acetal resins; polyethylene vinyl alcohol; polyesters such as polyethylene terephthalate (PET), polyethylene naphthalate, polytrimethylene terephthalate, poly(1,4-cyclohexylene dimethylene terephthalate) (PCT), polycarbonates; and aliphatic polyesters such as polylactic acid (PLA); polyphenylene sulfide; thermoplastic elastomers; polyacrylonitrile; cellulose and cellulose derivatives; polyaramids; acetals; fluoropolymers; regenerated cellulose fibers (rayons); copolymers and terpolymers thereof and mixtures or blends thereof, and without regard as whether a given polyolefin is syndiotacic, eutectic, isotactic, or atactic.

Specific examples of aliphatic polyesters operative in the present invention include fiber forming polymers formed from a combination of an aliphatic glycol such as ethylene glycol, propylene glycol, butylene glycol, hexanediol, octanediol or decanediol) or an oligomer of ethylene glycol (e.g., diethylene glycol or triethylene glycol) with an aliphatic dicarboxylic acid such as succinic acid, adipic acid, hexanedicarboxylic acid or decaneolicarboxylic acid); or the self-condensation of hydroxy carboxylic acids other than poly(lactic acid), such as polyhydroxy butyrate, polyethylene adipate, polybutylene adipate, polyhexane adipate, and copolymers containing the same. Aromatic polyesters operative in the present invention include fiber forming polymers formed from polyesters of alkylene glycols having 2-10 carbon atoms and aromatic diacids; polyalkylene naphthalates, which are polyesters of 2,6-naphthalenedicarboxylic acid and alkylene glycols, as for example polyethylene naphthalate; or polyesters derived from 1,4-cyclohexanedimethanol and terephthalic acid, as for example polycyclohexane terephthalate. Exemplary polyalkylene terephthalates include polyethylene terephthalate (also PET) and polybutylene terephthalate.

The present invention attempts to retain the processing and performance properties of the native polymer while imparting the ability to render the fiber and articles formed therefrom X-ray, metal detector, or magnetic anomaly detectable indicia that are rendered with iron rich ink. It is appreciated that the ink may also be detected with the inclusion of iron oxides or iron nitrides or in the form of a ferritic or martensitic stainless steel that is detectable by magnetic induction coil detectors. It is appreciated that stainless steel is approved for contact in a variety of food and pharmaceutical manufacturing processes. X-ray detection associated with food and pharmaceutical manufacturing processes is accomplished with stable barium compounds such as barium metal or barium sulfate.

In certain embodiments, each of the polymeric components of an inventive fiber includes other substances known conventionally to modify a processing property or performance property. Such additive substances illustratively include antioxidants, stabilizers, surfactants, waxes, flow promoters, solid solvents, dyes, pigments, plasticizers and combinations thereof.

The continuous filaments in certain inventive embodiments are mechanically crimped and cut into a desirable fiber length, thereby producing staple fiber. The length of the staple fibers typically ranges from 25 to 50 millimeters, although the fibers can be cut to any desired length outside this range.

The multi-component fibers of the invention can be staple fibers, continuous filaments, or meltblown fibers. In general, staple fibers, multifilament, and spunbond fibers formed in accordance with the present invention can have a fineness of 0.1 to 500 microns per filament. Meltblown filaments can have a fineness of 0.1 to 500 microns. Monofilament fibers can have a fineness of 0.1 to 500 microns.

The wipe is rendering sanitizing through inclusion of antimicrobial compounds that illustratively quaternary ammonium compounds, triclosan, triclocarban, hypochlorite, quat-alcohols, chloroxylenol, or combinations thereof. A wipe sanitizing solution also further includes softeners, lotions, or perfume to adjust the tactile properties. Preservatives such as methylisothiazolinone are used to prevent bacterial or fungal growth in the package. To render the inventive iron-based indicia compatible with sanitizing solution, the iron-based pigment is applied to a fiber substrate with a binder that upon drying encapsulates the pigment particulate to inhibit interaction between the iron-based pigmented indicia and the sanitizing solution.

With reference to FIG. 1, an inventive wipe is shown generally at 10, the wipe 10 has a polymer component substrate 12 based on fibers as detailed above. The substrate 12 has indicia 14 printed thereon. The indicia 14 includes an iron-based pigment in a binder that is encapsulating.

A binder operative herein illustratively includes acrylics, polyurethane acrylates, styrene acrylic copolymer, synthetic rubber latex, butylated melamine formaldehyde resins, and combinations thereof. Without intending to be bound to a particular theory, it is believed that the binder operates to binds the detectable particulate to the fabric by forming a transparent soft and rigid film on the fibers containing the particulate.

The indicia 14 is applied by conventional techniques to a dry substrate 12, prior to applying the sanitizing solution thereto.

A package is also provided that includes multiple inventive wipes in a container that is selectively sealable such that when sealed inhibits a sanitizing solution from evaporating from said container. In certain inventive embodiments, the container is formed of polymeric material that is itself metal detectable in the use environment. A detectable container is readily formed according to U.S. Pat. No. 8,980,982 B2.

Figure 2:
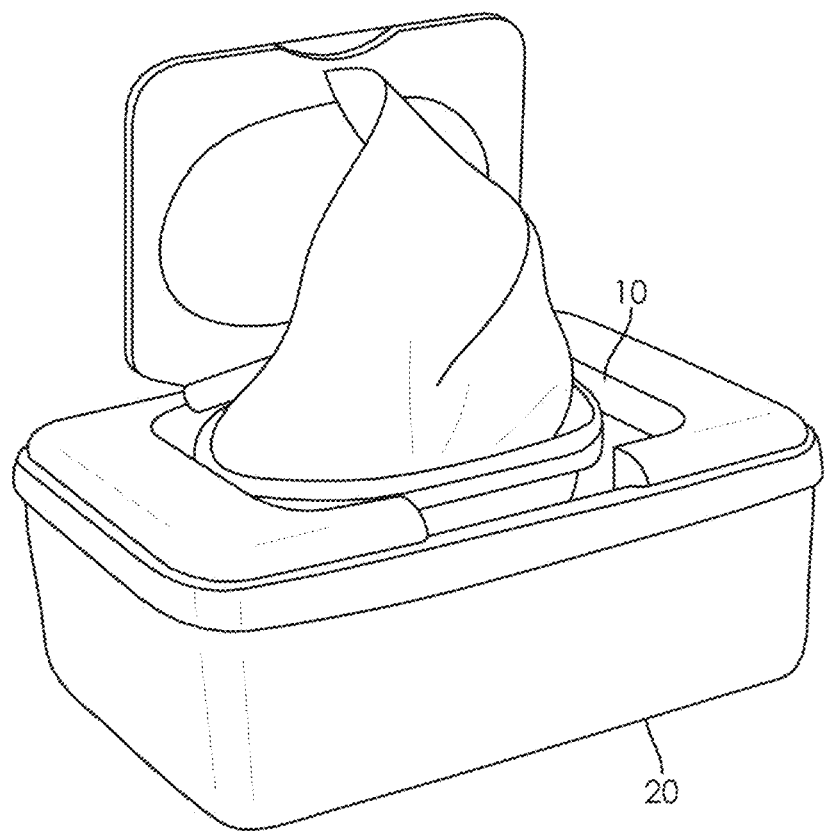
FIG. 2 is a schematic of a metal detectable plastic container containing an inventive metal detectable sanitizing wipe.

As shown in FIG. 2, a package 20 is formed of a thermoplastic loaded with detectable particulate so as to render the package detectable with a metal detector orthogonal response on a Loma IQ3+ balanced coil metal detector. As a result, accidental loss of the package 20 into a production line, or the wipes 10 as detailed above with respect to FIG. 1 can be located in a production stream. As a result, a precautionary batch of production before and after the loss incident need not be discarded.

Modern metal detection is based on creating a magnetic field with a transmitter coil and two receiving coils wired in reverse. The resulting field is interrupted when a conductive or magnetic contaminant passes through the field. The contaminant is detected by measuring the change in voltage above the change in voltage of non-contaminated product. If a contaminant is detected, that product is rejected. Contaminants are generally categorized as sphere equivalents in millimeters. The sensitivity and throughput are machine dependent.

X-ray inspection is based on density. The higher the density of the object being examined; the more energy is absorbed. X-ray detection measures how much energy is absorbed by a product or contaminant. X-ray detection can detect contaminants such as glass or bone that a metal detector will not detect. X-ray detection can perform other quality functions outside the scope of product contamination. The present invention focuses on contaminant detection. The contaminants are generally categorized as sphere equivalents. The sensitivity and throughput are machine dependent. In a production setting, the X-ray detector or the magnetic detector is associated with a production line that can be stopped when an inventive scrim or sheet substrate is detected by way of detector signal in the production stream. As a result, the effects of the contamination event are mitigated. Alternatively, a rejected product is shunted from the production line in response to the positive detector signal of contaminant being present.

The following example specific non-limiting examples of present invention. These examples should not be considered to be a limit on the scope of the appended claims.

Example 1

A padding liquor is formed including 70 grams per liter of styrene acrylic copolymer binder precursors in water, and 3 grams per liter of acid liberating agents such as diammonium phosphate or ammonium chloride which serve as catalysts in polymerization of the binder. Acetic Acid (30%) is titrated as needed to maintain a pH of 4.5-6.5 of the padding bath. The padding bath consists is then loaded with 20 grams per liter of particulate (430 series) having a Poisson size distribution and an average spherical particle size of 12 microns or iron oxide particles with a mean size of 5 microns and a generally spherical shape are dispersed in the padding liquor. The resulting padding liquor is pad printed onto polyester fabric sheeting in the shape of the desired indicia. The process can be repeated to build a desired loading of detectable particulate of 1 to 23 total weight percent particulate.

The fabric after padding is dried on conventional drying machinery such as hot air Stenter, hot floats dryers or steam heated cylinders. The dried goods subsequently cure for 5 to 15 minutes at 140 to 160° C. to complete fixation. The dried goods are then cut to form rectilinear wipes.

The finished wipes are then packaged in a sanitizing aqueous solution containing alkyl dimethyl benzyl ammonium chloride as the active agent and operate as a conventional sanitizing wipe.

Example 2

The resulting wipe of Example 1 is readily sensed by metal detector orthogonal response on a Loma IQ3+ balanced coil metal detector as a single ply.

The foregoing description is illustrative of particular embodiments of the invention, but is not meant to be a limitation upon the practice thereof. The following claims, including all equivalents thereof, are intended to define the scope of the invention.

The invention claimed is:

1. An article comprising:
   a substrate;
   an aqueous sanitizing solution absorbed into said substrate; and
   indicia printed on only a portion of said substrate, said indicia printed with an ink that includes detectable particulate loadings of iron oxide, iron nitrides, or forms of ferritic or martensitic stainless steel in a cured binder, the detectable particulate loadings present in an amount detectable in a single ply of said substrate by an in-line manufacturing production magnetic induction coil metal detector, the detectable particulate loadings being from 1 to 23 total weight percent of said substrate;
   wherein the binder is an acrylic, a polyurethane acrylate, a styrene acrylic copolymer, a butylated melamine formaldehyde resin, or a combination thereof that encapsulates the detectable particulate loadings to inhibit interaction between the indicia and said aqueous sanitizing solution, rendering said ink compatible with storage exposure to said aqueous sanitizing solution absorbed into said substrate.

2. The article of claim 1 wherein said ink additionally includes at least one of aluminum, copper, barium sulfate, or a combination of any of the aforementioned.

3. The article of claim 1 wherein said substrate is formed as a nonwoven material that is spun-laced, melt blown, spunbond, or a composite of two or more of these fiber formations.

4. The article of claim 1 wherein said substrate is comprised of polymer fiber that is one of polypropylene, polyethylene, polybutene, polyisobutylene, a polyamide, a polyacrylate, a polystyrene, a polyurethane, an acetal resin, a polyethylene vinyl alcohol; a polyester, a polyphenylene sulfide, a thermoplastic elastomers, a polyacrylonitrile; a cellulose, a polyaramid, or a block copolymer containing at least one of the aforementioned.

5. A package comprising:
   a plurality of the article of claim 1; and
   a resealable container that when sealed inhibits said aqueous sanitizing solution from evaporating from said container.

6. The package of claim 5 wherein said container is detectable by said in-line manufacturing production magnetic induction coil metal detector.

7. A process of detecting a fabric article comprising:
   forming an article of claim 1;
   passing the article through an in-line X-ray detector, metal, or a magnetic detector in a manufacturing facility; and
   collecting a signal from said X-ray detector, metal, or said magnetic detector indicative of the presence of the article.

8. The process of detecting the article of claim 7 wherein said article is a wipe.

9. The process of detecting the article of claim 7 wherein said X-ray detector, metal detector, or said magnetic detector is associated with a production line.

10. The process of detecting the article of claim 9 further comprising stopping said production line in response to the signal.

11. The process of detecting the article of claim 10 further comprising shunting product as rejected in response to the signal from said production line.

12. The article of claim 1 wherein said aqueous sanitizing solution includes quaternary ammonium compounds, triclosan, triclocarban, hypochlorite, quat-alcohols, chloroxylenol, or a combination thereof.

13. The article of claim 1 wherein the detectable particulate loadings comprise the ferritic or martensitic stainless steel.

14. The article of claim 1 wherein the detectable particulate loadings are present from 3 to 23 total weight percent of said substrate.

* * * * *